US012653837B2

(12) United States Patent
Quinn et al.

(10) Patent No.: US 12,653,837 B2
(45) Date of Patent: Jun. 16, 2026

(54) USE OF INHALED NITRIC OXIDE AND OXYGEN FOR THE TREATMENT OF PULMONARY HYPERTENSION

(71) Applicant: Bellerophon Pulse Technologies LLC, Warren, NJ (US)

(72) Inventors: Deborah Quinn, Morristown, NJ (US); Parag Shah, Morristown, NJ (US)

(73) Assignee: Malinckrodt Pharmaceuticals Ireland Limited, Dublin (IE)

( * ) Notice: Subject to any disclaimer, the term of this patent is extended or adjusted under 35 U.S.C. 154(b) by 0 days.

(21) Appl. No.: 16/961,886

(22) PCT Filed: Dec. 28, 2018

(86) PCT No.: PCT/US2018/067793
§ 371 (c)(1),
(2) Date: Jul. 13, 2020

(87) PCT Pub. No.: WO2019/133776
PCT Pub. Date: Jul. 4, 2019

(65) Prior Publication Data
US 2020/0360425 A1 Nov. 19, 2020

Related U.S. Application Data

(60) Provisional application No. 62/611,316, filed on Dec. 28, 2017.

(51) Int. Cl.
| | |
|---|---|
| *A61K 33/00* | (2006.01) |
| *A61K 9/00* | (2006.01) |
| *A61M 16/12* | (2006.01) |
| *A61P 11/00* | (2006.01) |

(52) U.S. Cl.
CPC .............. *A61K 33/00* (2013.01); *A61K 9/007* (2013.01); *A61M 16/12* (2013.01); *A61P 11/00* (2018.01); *A61M 2202/0208* (2013.01); *A61M 2202/0275* (2013.01)

(58) Field of Classification Search
CPC .................. A61K 9/007; A61M 16/12; A61M 2202/0208; A61M 2202/0275
See application file for complete search history.

(56) References Cited

U.S. PATENT DOCUMENTS

| | | | | |
|---|---|---|---|---|
| 2008/0051882 A1 * | 2/2008 | Rubin | ..................... | A61L 31/16 623/1.42 |
| 2017/0165447 A1 * | 6/2017 | Dasse | .................... | A61K 33/00 |
| 2017/0232166 A1 * | 8/2017 | Potenziano | ........ | A61B 5/02007 600/17 |

OTHER PUBLICATIONS

Behr, J et al. "Pulmonary hypertension in interstitial lung disease" Eur Respir J 2008; 31: 1357-1367 (Year: 2008).*
Pochis, W.T. et al. "Idiopathic pulmonary fibrosis. A rare cause of scintigraphic ventilation-perfusion mismatch" Clin Nucl Med. May 1990;15(5):321-3 (Year: 1990).*
Yoshida, M. et al. "The effect of low-dose inhalation of nitric oxide in patients with pulmonary fibrosis" Eur Respir J 1997; 10: 2051-2054 (Year: 1997).*

* cited by examiner

*Primary Examiner* — Andrew S Rosenthal
(74) *Attorney, Agent, or Firm* — Servilla Whitney LLC

(57) ABSTRACT

Described herein are methods of using inhaled nitric oxide for treating pulmonary hypertension, improving exercise capacity and/or reducing oxygen desaturation in a patient.

13 Claims, No Drawings

USE OF INHALED NITRIC OXIDE AND OXYGEN FOR THE TREATMENT OF PULMONARY HYPERTENSION

CROSS-REFERENCE TO RELATED APPLICATIONS

This application is the National Stage entry of PCT/US2018/067793, filed on Dec. 28, 2018, which claims priority to U.S. Provisional Application. Ser. No. 62/611,316, filed Dec. 28, 2017, the entire disclosures of which are hereby incorporated by reference herein.

TECHNICAL FIELD

Principles and embodiments of the present invention generally relate to the field of inhaled nitric oxide delivery.

BACKGROUND

Hypoxemia can occur in pulmonary arterial hypertension (PAH). The Reveal Registry showed 60% of PAH subjects use oxygen therapy (Abstract Presentation by Hap Faber, Chest, 2016). Hypoxemia in PAH can be caused by a variety of mechanisms: ventilation-perfusion mismatch, reduced diffusing capacity, admixture of mixed venous blood with low oxygen saturation in the setting of decreased cardiac output, or the opening of an intrapulmonary or intracardiac shunting (Porteous and Fitz, 2014). Hypoxemia can lead to pulmonary artery vasoconstriction and worsen pulmonary hypertension. The Reveal Registry showed that PAH patients with the lowest diffusion capacity of carbon monoxide (DLCO, a measure of the passage of oxygen from the air sacs to the pulmonary vessels)<40% when treated with oxygen therapy had a better survival.

Accordingly, there is a need for new therapies to improve oxygenation in patients with pulmonary hypertension (PH) such as PAH.

SUMMARY

One aspect of the present invention pertains to a method of reducing oxygen desaturation in a patient with PH.

Another aspect of the present invention pertains to a method of treating PH.

Another aspect of the present invention pertains to a method of treating PH by reducing oxygen desaturation.

Another aspect of the present invention pertains to a method of improving exercise capacity in a patient with PH.

Another aspect of the present invention pertains to a method of improving exercise capacity in a patient with PH by reducing oxygen desaturation.

In one or more embodiments, the patient is administered an effective amount of inhaled nitric oxide (iNO) in combination with an effective amount of long-term oxygen therapy (LTOT).

In one or more embodiments, the iNO is administered to the patient during the first half of inspiration.

In one or more embodiments, the effective amount of iNO is in the range of about 5 to about 300 micrograms NO per kilogram ideal body weight per hour (mcg/kg IBW/hr). In one or more embodiments, the effective amount of iNO is in the range of about 30 to about 100 mcg/kg IBW/hr, such as about 75 mcg/kg IBW/hr.

In one or more embodiments, the iNO is administered for a certain minimum treatment time, such as about 1, about 2, about 3, about 4, about 5, about 6 or about 7 days, or about 1, about 2, about 3, about 4, about 5, about 6, about 7 or about 8 weeks, or about 1, about 2, about 3, about 4, about 5, about 6, about 7, about 8, about 9, about 10, about 12, about 18 or about 24 months.

In one or more embodiments, the iNO is administered for a certain amount of time each day, such as at least about 1, about 2, about 3, about 4, about 5, about 6, about 7, about 8, about 9, about 10, about 11, about 12, about 16, about 18 or about 24 hours a day.

In one or more embodiments, the patient has a low, intermediate, or high probability of PH.

In one or more embodiments, the PH comprises one or more of PAH (WHO Group I), PH associated with left heart disease (WHO Group 2), PH associated with lung disease and/or chronic hypoxemia (WHO Group 3), chronic thromboembolic pulmonary hypertension (WHO Group 4) or PH with unclear multifactorial mechanisms (WHO Group 5).

In one or more embodiments, the patient has PAH.

In one or more embodiments, the patient has WHO Group 3 PH associated with interstitial lung disease (PH-ILD).

In one or more embodiments, the patient has WHO Group 3 PH associated with idiopathic pulmonary fibrosis (PH-IPF).

In one or more embodiments, the patient has WHO Group 3 PH associated with chronic obstructive pulmonary disease (PH-COPD).

In one or more embodiments, the patient has PH associated with pulmonary edema from high altitude sickness.

In one or more embodiments, the patient has PH associated with sarcoidosis.

In one or more embodiments, the patient has a ventilation-perfusion (V/Q) mismatch.

In one or more embodiments, a plurality of pulses of a gas comprising NO is administered to the patient over a plurality of breaths.

In one or more embodiments, the gas comprising NO is not administered to the patient in at least one breath of the plurality of breaths.

In one or more embodiments, the maximum time period between successive pulses of the gas comprising NO does not exceed about 30, about 25, about 20, about 15, about 14, about 13, about 12, about 11, about 10, about 9, about 8.5, about 8, about 7.5, about 7, about 6.5 or about 6 seconds.

In one or more embodiments, the maximum number of consecutive skipped breaths does not exceed three, two or one breaths.

In one or more embodiments, the average time period between successive pulses of the gas comprising NO does not exceed about 25, about 20, about 15, about 14, about 13, about 12, about 11, about 10, about 9, about 8.5, about 8, about 7.5, about 7, about 6.5 or about 6 seconds.

In one or more embodiments, the average time period between successive pulses of the gas comprising NO does not exceed about 3, about 2.5, about 2, about 1.5 or about 1 breaths.

In one or more embodiments, at least about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 625, about 650, about 700, about 750, about 800, about 850, about 900, about 950 or about 1000 pulses of the gas comprising NO is administered to the patient every hour.

In one or more embodiments, the administration of iNO provides an average decrease in the reduction of peripheral capillary oxygen saturation (SpO2) during exercise in a group of patients after 16 weeks of iNO administration of at least 1.

In one or more embodiments, the administration of iNO provides an average decrease in the reduction of SpO2 during exercise in a group of patients after 16 weeks of iNO administration of about 3.36.

In one or more embodiments, the administration of iNO provides an average increase in six-minute walk distance (6MWD) exercise in a group of patients after 16 weeks of iNO administration of at least 10 meters.

In one or more embodiments, the administration of iNO provides an average increase in 6MWD in a group of patients after 16 weeks of iNO administration of about 52.4 meters.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

It has surprisingly been discovered that long-term iNO therapy used in combination with LTOT maintains and/or improves exercise capacity and oxygen desaturation during exercise in patients with PH. It has also surprisingly been discovered that long-term iNO therapy used without LTOT actually leads to deterioration in oxygen desaturation and exercise capacity in these patients.

While not wishing to be bound by any particular theory, it is believed that iNO has a dual mechanism of action in PAH: lowering the pulmonary artery pressures and improving V/Q matching (Olchewski, et al, 1999). As described in more detail below, a Phase II trial unexpectedly found that only PAH subjects who used LTOT had benefits from iNO therapy, whereas PAH subjects on iNO therapy alone had deterioration in exercise capacity and oxygen desaturation during exercise. This difference in efficacy may be related to subjects with LTOT have lower DLCO and higher degrees of V/Q mismatch, therefore in these subjects the improved V/Q matching with iNO may be an important mechanism of action. These data support the importance of V/Q matching in this population of PAH subjects.

Accordingly, various aspects of the present invention pertain to the use of iNO therapy in combination with LTOT. Such use of iNO and LTOT can be used to treat PH, improve exercise capacity and/or improve oxygen desaturation.

Maintenance and/or improvements in oxygen desaturation can be assessed by many measurements. Oxygen saturation is an indication of how much hemoglobin in the blood is bound to oxygen, and is typically provided as a percentage of oxyhemoglobin to the total hemoglobin. SpO2 is an indication of oxygen saturation in the peripheral capillaries. Exemplary methods to measure SpO2 include, but are not limited to, pulse oximetry. Other parameters can also be used to assess oxygenation, such as arterial oxygen saturation (SaO2) and/or partial pressure of oxygen in arterial blood (PaO2). Oxygen desaturation refers to a drop in oxygen saturation, such as a drop in oxygen saturation after the patient performs a test assessing exercise capacity.

Maintenance and/or improvements in exercise capacity can be assessed by many measurements. One approach to assess exercise capacity is the six-minute walk test, which provides the 6MWD. Other measurements that can be used to assess exercise capacity include, but are not limited to, shuttle walk test, activity level, forced exercise, maximal exercise test, treadmill, bicycle and cardiopulmonary exercise test.

Accordingly, in one or more embodiments, the iNO therapy maintains or improves one or more parameters related to oxygen saturation and/or exercise capacity. In some embodiments, maintenance of a parameter corresponds to no change in that parameter over a certain time period. In some embodiments, if a parameter is expected to worsen in an untreated patient over time (e.g. 6MWD is expected to decrease in untreated PH patients), then maintenance of a parameter also includes a clinical worsening of the parameter that is a smaller magnitude than the clinical worsening that is expected for an untreated patient.

In one or more embodiments, the iNO therapy maintains or decreases oxygen desaturation (e.g. change in SpO2) over a certain time period, such as after administering iNO for 2, 3, 4, 5, 6, 7, 8, 9, 10, 15, 20, 25, 30 days 1, 2, 3, 4, 5, 6, 7, 8, 9, 10, 11, 12, 13, 14, 15 or 16 weeks or 1, 2, 3, 4, 5, 6, 7, 8, 9, 10, 12, 18 or 24 months or at least 1, 2, 3, 4 or 5 years.

In one or more embodiments, the patient's oxygen desaturation does not change during iNO therapy, even though the oxygen desaturation is expected to increase in an untreated patient. In other embodiments, a patient's oxygen desaturation is decreased over a certain time period. Exemplary decreases in oxygen desaturation include decreases of about 0.1, about 0.2, about 0.3, about 0.4, about 0.5, about 0.6, about 0.7, about 0.8, about 0.9, about 1, about 1.5, about 2, about 2.5, about 3, about 3.5, about 4, about 5, about 6, about 7, about 8, about 9 or about 10.

In one or more embodiments, 16 weeks of iNO therapy provides an average decrease in the reduction of SpO2 during exercise in a group of patients of at least about 1. In various embodiments, the average decrease in the reduction of SpO2 during exercise in the group of patients after 16 weeks of iNO therapy is at least about 1, about 2, about 3 or about 4, such as about 3.36.

In one or more embodiments, the iNO therapy maintains or increases exercise capacity (e.g. 6MWD) over a certain time period, such as after administering iNO for at least 2, 3, 4, 5, 6, 7, 8, 9, 10, 15, 20, 25 or 30 days or at least 1, 2, 3, 4, 5, 6, 7, 8, 9, 10, 11, 12, 13, 14, 15 or 16 weeks or at least 1, 2, 3, 4, 5, 6, 7, 8, 9, 10, 12, 18 or 24 months or at least 1, 2, 3, 4 or 5 years.

In one or more embodiments, the patient's exercise capacity does not change during iNO therapy, even though the exercise capacity is expected to decrease in an untreated patient. In other embodiments, a patient's exercise capacity is increased over a certain time period. Exemplary increases in 6MWD include increases of about 1, about 2, about 3, about 4, about 5, about 6, about 7, about 8, about 9, about 110, about 15, about 20, about 25, about 30, about 35, about 40, about 45, about 50, about 55 about 60 meters, about 70, about 80, about 90 or about 100 meters. Exemplary increases in exercise capacity (e.g. 6MWD) can also be expressed in percentages, such as increases of about 5, about 10, about 15, about 20, about 25, about 30, about 35, about 40, about 45, about 50, about 55, about 60, about 65, about 70, about 80, about 90 or about 100%.

In one or more embodiments, 16 weeks of iNO therapy provides an average increase in 6MWD in a group of patients after of at least about 10 meters. In various embodiments, the average increase in 6MWD in the group of patients after 16 weeks of iNO therapy is at least about 10, about 15, about 20, about 25, about 30, about 35, about 40, about 45, about 50, about 55 or about 60 meters, such as about 52.4 meters.

In one or more embodiments, 16 weeks of iNO therapy provides an average increase in 6MWD in a group of patients of at least about 5%. In various embodiments, the average increase in 6MWD in the group of patients after 16 weeks of iNO therapy is at least about 5, about 10, about 15, about 20, about 25, about 30, about 35, about 40, about 45, about 50, about 55, about 60, about 65, about 70, about 80, about 90 or about 100%.

In one or more embodiments, the patient or group of patients are diagnosed with PH. The patient(s) can be diagnosed by a cardiologist, pulmonologist or other physician according to suitable criteria using techniques such as echocardiography, right heart catheterization, etc. Examples of such criteria include, but are not limited to, patients that have a mean pulmonary arterial pressure (mPAP) at rest of at least 25 mm Hg, or a tricuspid regurgitation velocity greater than 2.9 m/s, or other combinations of factors as determined by an appropriate physician. The World Health Organization (WHO) has defined five categories of PH: PAH (WHO Group 1); PH associated with left heart disease (WHO Group 2), PH associated with lung disease and/or chronic hypoxemia (WHO Group 3), chronic thromboembolic pulmonary hypertension (WHO Group 4) or PH with unclear multifactorial mechanisms (WHO Group 5).

Examples of WHO Group 2 patients include those with systolic dysfunction, diastolic dysfunction and/or valvular disease.

Examples of WHO Group 3 patients include PH-COPD patients and those with interstitial lung disease (ILD) such as PH-IPF patients. Other examples of WHO Group 3 patients include those with combined pulmonary fibrosis and emphysema (CPFE), chronic high altitude exposure, or other lung diseases such as sleep disordered breathing or developmental diseases. COPD, ILD and other lung diseases can be diagnosed according to any suitable factor or combination of factors, such as those set forth in the guidelines of the American Thoracic Society. One exemplary set of criteria for diagnosing COPD is the Global initiative for chronic Obstructive Lung Disease (GOLD) criteria. In at least one embodiment, the patient has PH-COPD. In at least one embodiment, the patient has PH and ILD, such as a patient with PH-IPF. In at least one embodiment, the patient has PH associated with pulmonary edema from high altitude sickness.

Examples of WHO Group 5 patients include those with hematologic disorders, systemic disorders that have lung involvement (e.g. sarcoidosis, Langerhans cell histiocytosis, lymphangioleiomyomatosis, neurofibromatosis and vasculitis), metabolic disorders (e.g. thyroid disorders and glycogen storage disease), and other diseases such as tumor obstruction or renal failure. In at least one embodiment, the patient has PH associated with sarcoidosis.

In one or more embodiments, the patient has a V/Q mismatch.

In one or more embodiments, the patient or group of patients has a low, intermediate, or high probability of PH as determined by echocardiography or other suitable technique. One exemplary set of criteria for evaluating the probability of PH is set forth in the 2015 ESC/ERS Guidelines for Diagnosis and Treatment of Pulmonary Hypertension. In at least one embodiment, the patient has a low echocardiographic probability of PH. In at least one embodiment, the patient has a moderate echocardiographic probability of PH. In at least one embodiment, the patient has a high echocardiographic probability of PH.

The iNO may be administered continuously, or by a series of pulses, or any other suitable technique for delivering iNO to a patient's lungs. Exemplary devices for the administration of iNO are described in U.S. Pat. Nos. 5,558,083; 7,523,752; 8,757,148; 8,770,199; 8,893,717, 8,944,051; U.S. Pat. App. Pub. No. 2013/0239963; U.S. Pat. App. Pub. No. 2014/0000596; and U.S. Pat. App. Pub. No. 2016/0106949, the disclosures of which are hereby incorporated by reference in their entireties.

In one or more embodiments, iNO is administered by a NO delivery device utilizing cylinders containing NO and a carrier gas such as nitrogen ($N_2$). Exemplary NO cylinder concentrations include, but are not limited to, concentrations in the range of about 100 ppm to about 15,000 ppm, such as about 100, about 200, about 300, about 400, about 500, about 600, about 700, about 800, about 900, about 1000, about 1500, about 2000, about 2500, about 3000, about 3500, about 4000, about 4500, about 5000, about 6000, about 7000, about 8000, about 9000, about 10,000 or about 15,000 ppm. In one or more embodiments, the NO cylinder concentration is about 4880 ppm.

In one or more embodiments, the NO is generated bedside or at the point of administration. For example, various chemical reactions can be used to generate NO, such as reacting $N_2$ and oxygen ($O_2$) in the presence of an electrode, or reacting nitrogen dioxide ($NO_2$) with a reducing agent.

In one or more embodiments, the iNO is administered as a series of pulses. The iNO may have a specific pulse volume, such as about 0.1, about 0.2, about 0.3, about 0.4, about 0.5, about 0.6, about 0.7, about 0.8, about 0.9, about 1, about 1.5, about 2, about 3, about 4 or about 5 mL. The pulse volume may be the same from one breath to the next, or the pulse volume may vary according to the patient's breathing rate and/or the amount of iNO already delivered to the patient.

In one or more embodiments, the effective amount of iNO is in the range of about 5 to about 300 mcg/kg IBW/hr. A patient's ideal body weight correlates with the patient's estimated lung size, and is a function of the patient's sex and height. In various embodiments, the dose of iNO is about 5, about 10, about 15, about 20, about 25, about 30, about 35, about 40, about 45, about 50, about 55, about 60, about 65, about 70, about 75, about 80, about 85, about 90, about 95 or about 100 mcg/kg IBW/hr.

In one or more embodiments, a constant dose of iNO is delivered to the patient in each breath, such as a constant dose in nmol/breath, ng/breath or mL/breath. Exemplary doses include about 10, about 20, about 30, about 40, about 50, about 60, about 70, about 80, about 90, about 100, about 150, about 200, about 300, about 400, about 500, about 600, about 700, about 800, about 900, about 1,000 or about 1,500 nmol NO per breath.

In one or more embodiments, the iNO is administered continuously at a constant concentration. For example, the iNO may be administered at a constant concentration of about 1 ppm to about 100 ppm. In various embodiments, the dose of iNO is about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95 or about 100 ppm.

In one or more embodiments, a desired quantity of gas is administered to the patient over a plurality of breaths in a way that is independent of the patient's respiratory pattern. For example, a patient's iNO dose may be prescribed in terms of mcg/kg IBW/hr, such that a desired amount is delivered to the patient every hour regardless of the patient's respiratory pattern or breathing rate. The NO delivery device may have an input such as a dial, display, touchscreen or other user interface to receive the patient's prescription. An amount of NO per breath (e.g. nmol NO, ng NO, mL of gas comprising NO, etc.) can be calculated based on the patient's current respiratory pattern, and that amount of NO can be delivered to the patient in the next breath or for several breaths. The NO delivery device may monitor the patient's respiratory pattern or breathing rate (or changes in the respiratory pattern or breathing rate) and re-calculate and/or otherwise adjust the amount of NO-containing gas that is delivered on the current breath or on subsequent breaths. The NO delivery device can have a control system with appropriate software and/or hardware (e.g. flow sensors, pressure sensors, processors, memory, etc.) for monitoring the breath, calculating or otherwise determining the amount of NO to be delivered, and be in communication with other components of the NO delivery device (e.g. flow sensors, pressure sensors, valves, gas conduits, etc.) for delivering the gas comprising NO. The amount of NO per breath can be calculated and/or adjusted after every breath or can be calculated and/or adjusted at certain intervals such as every minute, every 10 minutes, every 10 breaths, every 100 breaths, etc.

In one or more embodiments, the iNO is not delivered to the patient every breath and at least one breath is skipped during the iNO therapy. The time period between individual pulses of gas comprising NO can vary or can be constant. In various embodiments, a maximum time period between pulses, a maximum average time period between pulses and/or a minimum pulse frequency may be provided.

Various situations can result in iNO being skipped in a particular breath. For example, an intermittent dosing regimen may be utilized in which the iNO is administered every $n^{th}$ breath, with n being greater than 1. In various embodiments, n is about 1.01, about 1.1, about 1.2, about 1.3, about 1.4, about 1.5, about 1.6, about 1.7, about 1.8, about 1.9, about 2, about 2.5, about 3, about 4, about 5, about 6, about 7, about 8, about 9 or about 10. When n is not a whole number (e.g. 1.1 or 2.5), n can represent an average over multiple breaths. As an example, administering iNO every 2.5 breaths indicates that iNO is administered an average of 2 breaths out of every 5 breaths (i.e. 5/2=2.5). Similarly, administering iNO every 1.1 breaths indicates that iNO is administered an average of 10 breaths out of every 11 breaths (i.e. 11/10=1.1). Similar calculations can be performed for other intermittent dosing regimens where iNO is administered every $n^{th}$ breath, with n being greater than 1.

In one or more embodiments, an intermittent dosing regimen may be utilized in which predetermined breaths are skipped. The skipping of predetermined breaths can be based on predetermined patterns such as skipping every other breath, skipping every third breath, skipping two consecutive breaths and delivering on the third breath, etc. The predetermined pattern can include delivering gas comprising NO on every $n^{th}$ breath, such as having n be greater than 1, for example about 1.01, about 1.1, about 1.2, about 1.3, about 1.4, about 1.5, about 1.6, about 1.7, about 1.8, about 1.9, about 2, about 2.5, about 3, about 4, about 5, about 6, about 7, about 8, about 9 or about 10.

In one or more embodiments, one or more breaths is skipped in a certain time period. For example, 1, 2, 3, 4, 5, etc. breaths may be skipped every hour, every 30 minutes, every 15 minutes, every 10 minutes, every minute, every 30 seconds, etc. In some embodiments, as little as one breath is skipped during the entire iNO therapy. In other embodiments, multiple breaths are skipped during iNO therapy.

In one or more embodiments, an intermittent dosing regimen may be utilized in which random breaths are skipped. The random breath skipping can be determined according to a random number generator and/or can be based on current clinical conditions such as the patient's respiratory pattern, the patient's breathing rate, the amount of iNO that has been delivered to the patient, the patient's iNO prescription, etc., and/or can be based on settings for the NO delivery device such as a minimum pulse volume.

In one or more embodiments, the NO delivery device may have a minimum quantity of gas that can be delivered in a breath, such as a minimum pulse volume. This minimum quantity of gas can be set by the user or can be a minimum threshold value set by the specifications of the NO delivery device. In one or more embodiments, when the quantity of gas comprising NO to be delivered to the patient in a particular breath is less than the minimum quantity of gas per breath (e g minimum pulse volume), administration of the gas is skipped for that breath. In one or more embodiments, when the breath is skipped, a new quantity of gas per breath is calculated and/or the quantity of gas is carried over and is added to the amount of gas to be delivered in one or more subsequent breaths.

In addition to the exemplary situations described above, other situations that can result in one or more breaths being skipped during iNO therapy are also encompassed by the present disclosure. Such situations include, but are not limited to, skipped breaths or a pause in iNO therapy due to: changing or switching the drug cylinder or cartridge; NO delivery device purging; engagement with other devices or delivery systems such as LTOT, continuous positive airway pressure (CPAP), bilevel positive airway pressure (BPAP), etc.; NO delivery device alarm conditions such as apnea, empty drug cylinder/cartridge, empty battery, etc.; or NO delivery device fault condition(s).

In one or more embodiments, there is a maximum time period between successive pulses of the gas comprising NO. For example, the time period between successive pulses may vary or may be constant, but an upper limit may be provided that prevents too long of a period between successive pulses of gas. In exemplary embodiments, the maximum time period between successive pulses of gas comprises NO does not exceed about 30, about 25, about 20, about 15, about 14, about 13, about 12, about 11, about 10, about 9, about 8.5, about 8, about 7.5, about 7, about 6.5 or about 6 seconds.

In one or more embodiments, the maximum time period between successive pulses of the gas comprising NO is provided as a maximum number of breaths. In exemplary embodiments, the maximum number of consecutive skipped breaths does not exceed four, three, two or one breaths.

In one or more embodiments, the average time period between successive pulses of the gas comprising NO does not exceed a certain time period, such as not exceeding about 30, about 25, about 20, about 15, about 14, about 13, about 12, about 11, about 10, about 9, about 8.5, about 8, about 7.5, about 7, about 6.5 or about 6 seconds. Again, the time period between individual pulses can vary or can be the same.

In one or more embodiments, the average number of consecutive skipped breaths does not exceed about 3, about 2.5, about 2, about 1.5, about 1 or about 0.5 breaths.

In one or more embodiments, the frequency of pulse administration is provided as a number of pulses in a given time period, such as pulses per hour. For example, in one or more embodiments the patient is administered at least about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 625, about 650, about 700, about 750, about 800, about 850, about 900, about 950 or about 1000 pulses of the gas comprising NO per hour.

Shorter durations may also be used, and these pulse frequencies can likewise be expressed in terms of pulses per minute or other time period. In one or more embodiments, the patient is administered at least about 5, about 5.1, about 5.2, about 5.3, about 5.4, about 5.5, about 5.6, about 5.7, about 5.8, about 5.9 about 6, about 6.1, about 6.2, about 6.3, about 6.4, about 6.5, about 6.6, about 6.7, about 6.8, about 6.9 about 7, about 7.1, about 7.2, about 7.3, about 7.4, about 7.5, about 7.6, about 7.7, about 7.8, about 7.9 about 8, about 8.1, about 8.2, about 8.3, about 8.4, about 8.5, about 8.6, about 8.7, about 8.8, about 8.9 about 9, about 9.5, about 10, about 10.5, about 11, about 11.5, about 12, about 12.5, about 13, about 13.5, about 14, about 14.5, about 15, about 16, about 17, about 18, about 19 or about 20 pulses per minute.

In one or more embodiments, the iNO is administered for a certain amount of time each day. For example, the iNO may be administered for at least about 1 hour a day. In various embodiments, the iNO is administered for at least about 1, about 2, about 3, about 4, about 5, about 6, about 7, about 8, about 9, about 10, about 11, about 12, about 16, about 18 or about 24 hours a day.

In one or more embodiments, the iNO is administered for a certain treatment time. For example, the iNO may be administered for at least 2 days. In various embodiments, the iNO is administered for at least about 2, about 3, about 4, about 5, about 6 or about 7 days, or about 1, about 2, about 3, about 4, about 5, about 6, about 7 or about 8 weeks, or about 1, about 2, about 3, about 4, about 5, about 6, about 7, about 8, about 9, about 10, about 12, about 18 or about 24 months, or 1, 2, 3, 4 or 5 years.

In one or more embodiments, the patient is also receiving long-term oxygen therapy (LTOT). In various embodiments, the LTOT is administered for at least about 1, about 2, about 3, about 4, about 5, about 6, about 7, about 8, about 9, about 10, about 11, about 12, about 16, about 18 or about 24 hours a day. In various embodiments, the LTOT is administered at a dose of about 0.5 L/min to about 10 L/min, such as about 0.5, about 1, about 1.5, about 2, about 2.5, about 3, about 4, about 5, about 6, about 7, about 8, about 9 or about 10 L/min. The LTOT may be administered continuously or via pulses.

EXAMPLES

Example 1—Effect of Long-Term iNO Therapy and LTOT on Oxygen Desaturation and Exercise Capacity in Patients with PAH This study was a Phase 2, placebo controlled, double-blind, randomized, clinical study to determine the safety, tolerability and efficacy of pulsed iNO versus placebo as add-on therapy in symptomatic subjects with PAH (IK-7001-PAH-201; NCT01457781). The primary outcome of this study was change from baseline in pulmonary vascular resistance (PVR). Secondary outcome measure included change in 6MWD, time to first clinical worsening event (TTCW), change in WHO functional class, change in Borg Dyspnea Score (BDS) and change in patient reported outcome (PRO) scores by the SF-36 short form version 2 and the Cambridge Pulmonary Hypertension Outcome Review (CAMPHOR).

PAH subjects were administered pulsed iNO at a dose of 25 or 75 mcg/IBW kg/hr for up to 24 hours a day for up to 16 weeks, or received pulsed placebo (99.999% $N_2$) for up to 24 hours a day for up to 16 weeks. The dose of 25 mcg/kg IBW/hr was administered from a mini-cylinder having 2,440 ppm NO and the dose of 75 mcg/kg IBW/hr was administered from a mini-cylinder having 4,880 ppm NO.

All subjects had a confirmed diagnosis of PAH at the time of baseline right heart catheterization (RHC) according to the following criteria: mean pulmonary arterial pressure (mPAP)≥25 mmHg at rest, with a concomitant mean pulmonary capillary wedge pressure (mPCWP), mean left atrial pressure (mLAP), or left ventricular end diastolic pressure (LVEDP)≤15 mmHg and a PVR≥240 dynes*sec*cm$^{-5}$. All subjects were 16 to 80 years old and had a 6MWD at least 100 meters and no greater than 450 meters. All subjects were receiving at least one approved PAH therapy and were clinically symptomatic from PAH (e.g. onset or increased dyspnea on exertion, dizziness, near-syncope, syncope, chest pain or peripheral edema).

Oxygen desaturation was measured as the drop in SpO2 level from the beginning to the end of the six-minute walk test (6MWT). Oxygen desaturation was measured at baseline and after 16 weeks of chronic treatment with iNO at a dose of 75 mcg/kg IBW/hr (iNO 75) or 25 mcg/kg IBW/hr (iNO 25) or placebo. Data is last observation carried forward for those that did not complete 16 weeks of treatment.

Table 1 below shows the change in oxygen desaturation for placebo, iNO 25 and iNO 75. Also shown is the change in exercise capacity, measured as the change in 6MWD from baseline to 16 weeks.

TABLE 1

| Dose | Change in Oxygen Desaturation (SpO2) | Change in 6MWD (meters) | Comment |
|---|---|---|---|
| Placebo | 0.14 | 7.5 | Minimal increase in desaturation with minimal change in 6MWD |
| iNO 25 | −0.14 | 4.7 | Minimal decrease in desaturation with minimal change in 6MWD |
| iNO 75 | −2.19 | 22.8 | Measurable decrease in desaturation and increase in 6MWD |

As seen in Table 1, only the iNO 75 dose showed a meaningful decrease in oxygen desaturation as well as an increase in 6MWD. Further evaluation of the iNO 75 dose was conducted to assess the impact of combination with LTOT. These results are shown in Table 2.

TABLE 2

| Dose | Change in Oxygen Desaturation (SpO2) | Change in 6MWD (meters) | Comment |
|---|---|---|---|
| iNO 75 No LTOT | 0.40 | −20.8 | Measurable increase in desaturation and decrease in 6MWD |
| iNO 75 LTOT | −3.00 | 34.9 | Measurable decrease in desaturation and increase in 6MWD |

As seen in Table 2, the patients on iNO and LTOT showed improvements in oxygen desaturation and exercise capacity. However, patients that received iNO without oxygen showed no improvement in either category. Surprisingly, both parameters showed deterioration, indicating iNO alone did not have therapeutic effect.

A further evaluation was performed comparing using only those patients who were compliant with iNO therapy, to ensure the lack of effect seen in the non-LTOT group was not due to lack of drug use. The criteria used for compliance was >12 hours per day of use. The results of this assessment are provided in Table 3.

TABLE 3

| Dose | Change in Oxygen Desaturation (SpO2) | Change in 6MWD (meters) | Comment |
|---|---|---|---|
| iNO 75 > 12 hrs; No LTOT | 1.33 | −29.7 | Measurable increase in desaturation and decrease in 6MWD |
| iNO 75 > 12 hrs; LTOT | −3.36 | 52.4 | Measurable decrease in desaturation and increase in 6MWD |

As seen in Table 3, the patients on LTOT who were compliant with the therapy showed large improvements in oxygen desaturation and exercise capacity. However, patients that were compliant with iNO without the added benefit of oxygen showed marked deterioration in both categories.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A method of reducing oxygen desaturation in a patient with WHO Group 3 pulmonary hypertension associated with idiopathic pulmonary fibrosis (PH-IPF), the method comprising:
    administering an effective amount of inhaled nitric oxide (iNO) in combination with an effective amount of long-term oxygen therapy (LTOT) to a patient in need thereof, wherein the iNO is administered at a dose of about 50 to about 100 mcg/kg IBW/hr for at least 6 hours a day for at least 4 weeks.

2. A method of treating WHO Group 3 pulmonary hypertension associated with idiopathic pulmonary fibrosis (PH-IPF), the method comprising:
    administering an effective amount of inhaled nitric oxide (iNO) in combination with an effective amount of long-term oxygen therapy (LTOT) to a patient in need thereof, wherein the iNO is administered at a dose of about 50 to about 100 mcg/kg IBW/hr for at least 6 hours a day for at least 4 weeks.

3. A method of improving exercise capacity in a patient with WHO Group 3 pulmonary hypertension associated with idiopathic pulmonary fibrosis (PH-IPF), the method comprising:
    administering an effective amount of inhaled nitric oxide (iNO) in combination with an effective amount of long-term oxygen therapy (LTOT) to a patient in need thereof, wherein the iNO is administered at a dose of about 50 to about 100 mcg/kg IBW/hr for at least 6 hours a day for at least 4 weeks.

4. The method of claim 2, wherein the iNO is administered to the patient during the first half of inspiration.

5. The method of claim 2, wherein the iNO is administered for at least 12 hours a day.

6. The method of claim 2, wherein the patient has a ventilation-perfusion (V/Q) mismatch.

7. The method of claim 2, wherein the iNO is administered for at least 3 months.

8. The method of claim 2, wherein the iNO is administered at a dose of about 50 mcg/kg IBW/hr to about 75 mcg/kg IBW/hr.

9. The method of claim 2, wherein the iNO is administered at a dose of about 75 mcg/kg IBW/hr.

10. The method of claim 2, wherein the administration of iNO provides an average decrease in the reduction of SpO2 during exercise in a group of patients after 16 weeks of iNO administration of at least 1.

11. The method of claim 2, wherein the administration of iNO provides an average decrease in the reduction of SpO2 during exercise in a group of patients after 16 weeks of iNO administration of about 3.36.

12. The method of claim 2, wherein the administration of iNO provides an average increase in six-minute walk distance (6MWD) exercise in a group of patients after 16 weeks of iNO administration of at least 10 meters.

13. The method of a claim 2, wherein the administration of iNO provides an average increase in six-minute walk distance (6MWD) in a group of patients after 16 weeks of iNO administration of about 52.4 meters.

* * * * *